(12) United States Patent
Yagihara et al.

(10) Patent No.: US 6,420,612 B1
(45) Date of Patent: Jul. 16, 2002

(54) BICYCLOHEPTENE DERIVATIVES AND PROCESSES FOR THE PREPARATION OF THE SAME

(75) Inventors: Tomio Yagihara; Hiroyuki Yamanaka, both of Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/936,580

(22) PCT Filed: Apr. 27, 2000

(86) PCT No.: PCT/JP00/02762

§ 371 (c)(1),
(2), (4) Date: Sep. 13, 2001

(87) PCT Pub. No.: WO00/66525

PCT Pub. Date: Nov. 9, 2000

(30) Foreign Application Priority Data

Apr. 28, 1999 (JP) .............................. 11-120951
Jul. 22, 1999 (JP) .............................. 11-174800

(51) Int. Cl.$^7$ .............................................. C07C 43/30

(52) U.S. Cl. ........................ 568/591; 562/508; 562/510; 562/502

(58) Field of Search ................................ 562/507, 508, 562/510, 502; 568/591

(56) References Cited

PUBLICATIONS

Mitcell et al, Tetrahedron Letters, 42(6) pp1741–1744, 1986.*
Hoch, Journal Organic Chemistry, 26, 2066–2072, 1961.*

\* cited by examiner

*Primary Examiner*—Paul J. Killos
*Assistant Examiner*—Hector Reyes
(74) *Attorney, Agent, or Firm*—Dennis G. LaPointe; Mason & Associates, PA

(57) ABSTRACT

Bicycloheptene compounds represented by general formula (1) and being useful as intermediates for the production of agricultural chemicals or drugs (wherein X is hydroxycarbonyl, hydroxymethyl, halogenomethyl, nitromethyl, or methylthiomethyl); and a process for the preparation of compounds of general formula (1), characterized by reacting 5,5-dimethoxy-1,2,3,4-tetrachlorocyclopentadiene with a compound represented by general formula (2) (wherein X is as defined above)

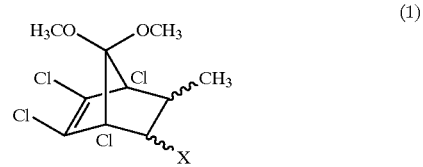

6 Claims, No Drawings

BICYCLOHEPTENE DERIVATIVES AND PROCESSES FOR THE PREPARATION OF THE SAME

TECHNICAL FIELDS

The present invention relates to novel bicycloheptane derivatives useful as intermediates for the production of agricultural chemicals, drugs and others, and to processes for the preparation of the same.

BACKGROUND ART

A Diels-Alder reaction of trans-methyl crotonate with 1,1-dimethoxy-2,3,4,5-tetrachlorocyclopentadiene is described in Tetrahedron 42, 1741–1744 (1986). It is reported that the addition product becomes a mixture of isomers that are difficult to separate by distillation. A reaction with ethyl crotonate is also described in J. Org. Chem., 26, 2066 (1961).

DISCLOSURE OF THE INVENTION

There are no reports in known documents, patents and others on a reaction with crotonaldehyde instead of methyl crotonate described in the above-mentioned paper. If the reaction is carried out under the same conditions as those described in the said paper, a main product is the trans-2 isomer, as shown in the following reaction scheme. The trans-1 and cis isomers, which are preferable to use as intermediates for producing herbicides, were obtained at low production rates. (A rough isomer ratio was trans-1:cis:trans-2=20:10:70.)

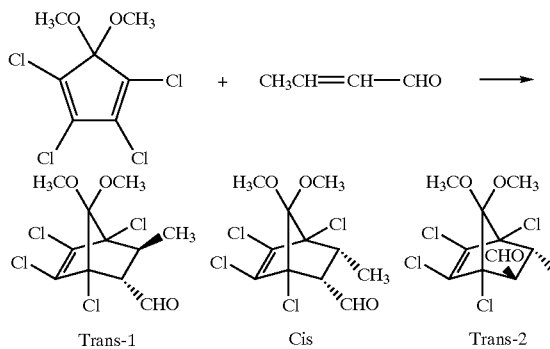

| Trans-1 | Cis | Trans-2 |

The present invention relates to novel bicycloheptane derivatives to become intermediates for the preparation of drugs, agricultural chemicals and others, and to processes for the production of the same. It is an object of the present invention to provide compounds to be used for the preparation of trans-1 and cis isomers suitable for the purposes in good yields, and industrially advantageous processes.

The trans-1 and cis isomers are compounds to be used as intermediates for the industrially advantageous production of bicycloheptene compounds represented by Formula (3)

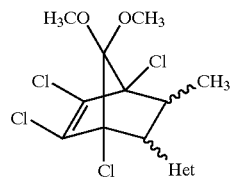

(3)

(wherein, Het is optionally substituted isoxazolyl or isoxazolidyl). The compounds of Formula (3) are useful as intermediates for the preparation of herbicides described in World Open WO 97/41117, WO 98/31681 and others.

The compounds of the present invention may have stereoisomers, depending on substituents at positions 5 and 6. The (1S, 4R, 5R, 6S) and (1R, 4S, 5S, 6R) isomers are represented by "trans" and (1S, 4R, SR, 6R) and (1R, 4S, 5S, 6S) isomers as "cis".

The present invention relates to compounds of Formula (1)

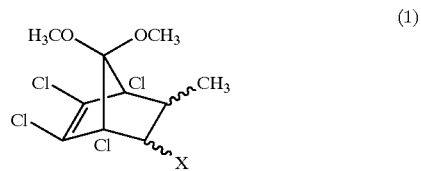

(1)

(wherein, X is hydroxycarbonyl, hydroxymethyl, halogenomethyl, nitromethyl or methylthiomethyl), and processes for the preparation of the said compounds of Formula (1) by reactions of 5,5-dimethoxy-1,2,3,4-tetrachlorocyclopentadiene with compounds of Formula (2)

$$CH_3CH=CH-X \qquad (2)$$

(wherein X is as defined above).

The processes of the present invention also give mixtures of trans and cis isomers, as shown in the following reaction scheme. However, the trans-2 isomer is produced at a very low

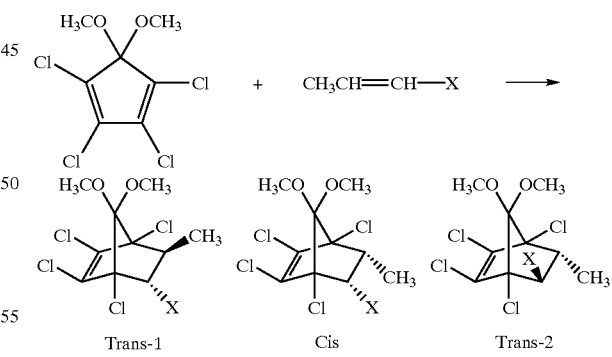

| Trans-1 | Cis | Trans-2 | rate, as described later in Examples. The compounds of the present invention are thus produced industrially advantageously.

FORMS TO IMPLEMENT THE INVENTION

Process 1
Preparation of trans-1,4,5,6-tetrachloro-3-methyl-7,7-dimethoxybicyclo[2.2.1]-hept-5-ene-2-carboxylic acid, where X is a carboxylic acid.

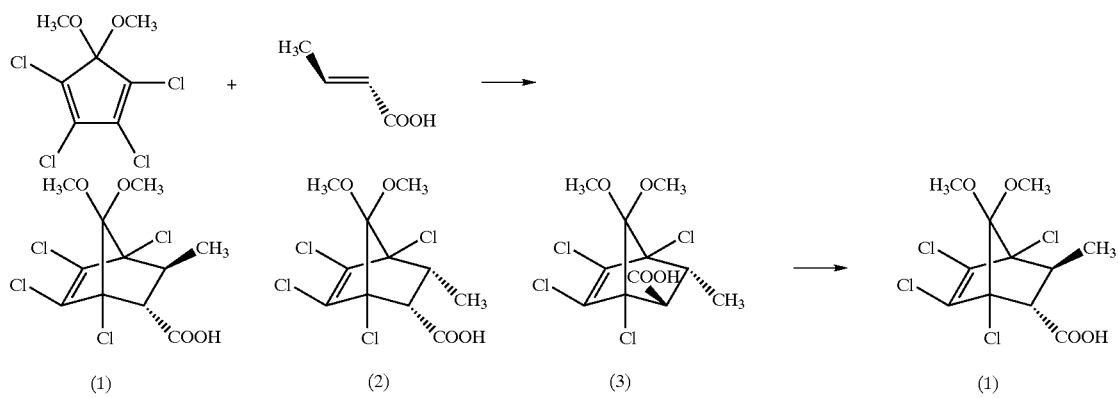

A Diels-Alder reaction of (E)-2-butenic acid and 5,5-dimethoxy-1,2,3,4-tetrachlorocyclopentadiene is carried out by heating at 120 to 160° C. without a solvent for 8 to 15 hours.

The reaction product consists of the main product of (1) and small amounts of Stereoisomers (2) and (3). Stereoisomer (1) is isolated by recrystallization of the reaction product. Examples of solvents to use for the recrystallization include general recrystallization solvents, such as n-hexane, acetone, ethyl acetate or their mixtures.

Process 2

Preparation of cis-1,4,5,6-tetrachloro-3-methyl-7,7-dimethoxybicyclo[2.2.1]-hept-5-ene-2-carboxylic acid, where X is a carboxylic acid.

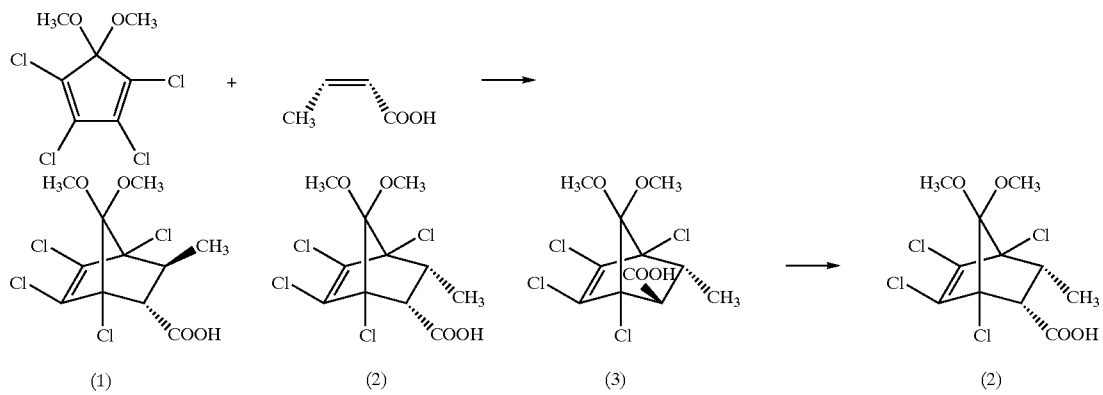

A Diels-Alder reaction of (Z)-2-butenic acid and 5,5-dimethoxy-1,2,3,4-tetrachlorocyclopentadiene is carried out by heating at 100 to 120° C. without a solvent for 8 to 15 hours.

The reaction product consists of the main product of (2) and small amounts of Stereoisomers (1) and (3). Stereoisomer (2) is isolated by recrystallization of the reaction product from a general recrystallization solvent, such as n-hexane, acetone, ethyl acetate or their mixture.

A mixture containing a larger amount of either the (E)-or (Z)-2-butenic acid can also be used as a starting material for Processes 1 and 2.

Process 3

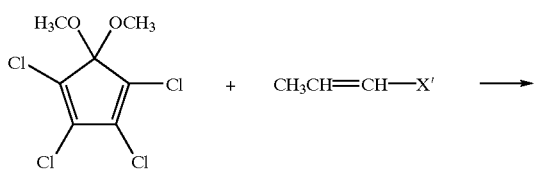

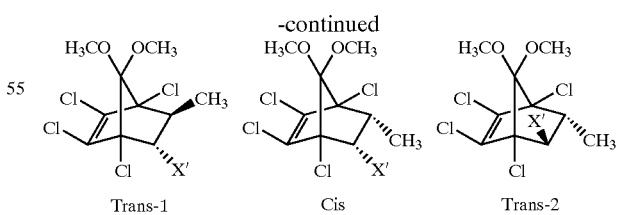

(wherein, X' is hydroxymethyl, halogenomethyl, nitromethyl or methylthiomethyl).

X of Compound (1) of the present invention can be any substituent that is oxidized to —CHO or nitrile oxide. Examples of X include hydroxymethyl, chloromethyl, bromomethyl, nitromethyl and methylthiomethyl.

A solvent may or may not be used for the reaction. A reaction temperature is about that necessary for the reaction to proceed, and is usually selected in the range between 100° C. and 200° C. Any solvent inert to the reaction can be used. Alcoholic solvents such as methoxy ethanol and amyl alcohol are preferred. A reaction time varies depending on compounds used. It takes about 5 hours to a week.

Usual wark-up after the completion of the reaction give target compounds.

Reaction products are identified by 1R, NMR, MS and other means.

Best Forms to Implement the Invention

The present invention is described in more detail in reference to Examples.

EXAMPLE 1
Preparation of trans-1,4,5,6-tetrachloro-3-methyl-7,7-dimethoxybicyclo[2.2.1]hept-5-ene-2-carboxylic acid 5.7 g of (E)-2-butenic acid and 20 g of 5,5-dimethoxy-1,2,3,4-tetrachlorocyclopentadiene were heated with stirring at 160° C. for 12 hours without a solvent. It was confirmed by NMR that the starting materials disappeared and addition products were formed. Then, an aqueous solution of sodium hydrogen carbonate was added to the reaction mixture, and chloroform was added to separate. The aqueous layer was adjusted to pH 1 with hydrochloric acid, and extracted with ethyl acetate. The ethyl-acetate layer was washed with saturated salt water, and dried over anhydrous magnesium sulfate. Ethyl acetate was distilled off under reduced pressure, to give 12.8 g of a crude product. An NMR spectrum showed that the product contained the isomers at a ratio of trans-1:cis:trans-2=82:10:8. The crude product was recrystallized from n-hexane:ethyl acetate=4:1, to give 9.0 g of the title compound (m.p. 169–170° C.).

EXAMPLE 2
Preparation of cis-1,4,5,6-tetrachloro-3-methyl-7,7-dimethoxybicyclo[2.2.1]hept-5-ene-2-carboxylic Acid 1.5 g of 2-butenic acid (a mixture of (Z):(E)=75:25) and 5.24 g of 5,5-dimethoxy-1,2,3,4-tetrachlorocyclopentadiene were heated with stirring at 110° C. for 14 hours without a solvent. It was confirmed by NMR that the starting materials disappeared and addition products were formed. Then, the reaction mixture was treated in the same way as that of Example 1, to give 3.9 g of a crude product. An NMR spectrum showed that the product contained the isomers at a ratio of trans-1:cis=4:96. The crude product was recrystallized from n-hexane:ethyl acetate=4:1, to give 3.5 g of the title compound (m.p. 165–168° C.).

EXAMPLE 3
Preparation of 6-methyl-trans-5-hydroxymethyl-7,7-dimethoxy-1,2,3,4-tetrachlorobicyclo[2.2.1]hept-2-ene 3.7 g of 2-butene-1-ol and 15 g of 5,5-dimethoxy-1,2,3,4-tetrachlorocyclopentadiene were heated with stirring at 200° C. for 48 hours without a solvent. It was confirmed by NMR that the starting materials disappeared. (The reaction product contained the isomers at a ratio of trans-1:cis:trans-2=44:26:31.) Then, the reaction solution was returned to room temperature, and 100 mL of water was added. The resulting mixture was twice extracted with 50 mL of ethyl acetate and separated. The ethyl-acetate layer was washed with saturated salt water, and dried over anhydrous magnesium sulfate. Ethyl acetate was distilled off under reduced pressure. The residue of a crude product was purified with silica gel column chromatography (elution with n-hexane:ethyl acetate=95:5), to give 1.5 g of the title compound (m.p. 80–82° C.).

EXAMPLE 4
Preparation of 6-methyl-trans-5-chloromethyl-7,71-dimethoxy-1,2,3,4-tetrachlorobicyclo[2.2.1]hept-2-ene 3.0 g of 1-chloro-2-butene (a mixture of Z:E=1:6) and 10.0 of 5,5-dimethoxy-1,2,3,4-tetrachlorocyclopentadiene were heated with stirring at 170° C. for 5 days without a solvent.

The reaction product contained the isomers at a ratio of trans-1:cis:trans-2=57:24:19.

The reaction solution was treated in the same way as that of Example 3 and purified with silica gel column chromatography, to give 4.0 g of the tile compound as syrup. $n_D^{17}$: 1.5263

APPLICATION EXAMPLE 1
Preparation of trans-1,4,5,6-tetrachloro-3-methyl-7-oxobicyclo[2.2.1]hept-5-ene-2-carboxylic acid 2.0 g of trans-1,4,5,6-tetrachloro-3-methyl-7,7-dimethoxybicyclo[2.2.1]hept-5-ene-2-carboxylic acid obtained in Example 1 was stirred in 6.7 g of concentrated sulfuric acid at room temperature for 2 days. TLC confirmed the disappearance of the starting material. The reaction solution was poured into ice-water, and extracted with ethyl acetate. The extract was washed with saturated salt water, dried over anhydrous magnesium sulfate, and concentrated under reduced pressure, to give 1.7 g of the title compound. m.p. 166–167° C.

Industrial Applicability

The present invention provides compounds to be used for the industrially advantageous production of bicycloheptene compounds represented by Formula (3)

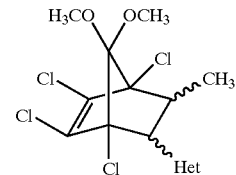

and having heterocyclic rings at position 5, which are useful as intermediates for the preparation of herbicides.

The compounds of the present invention can be derived to the said compounds of Formula (3) according to the method shown in the following scheme: The compound where X is hydroxyl is oxidized to an aldehyde (X=CHO), and further changed to an oxime with hydroxylamine, then to a nitrite oxide with an oxidizing agent, and further to Intermediate Z-1 by a reaction with ethylene.

The compound where X is chloromethyl, for example, is reacted with sodium nitrite in DMSO used as a solvent, and the produced nitrite oxide is reacted with ethylene to give Intermediate Z-1.

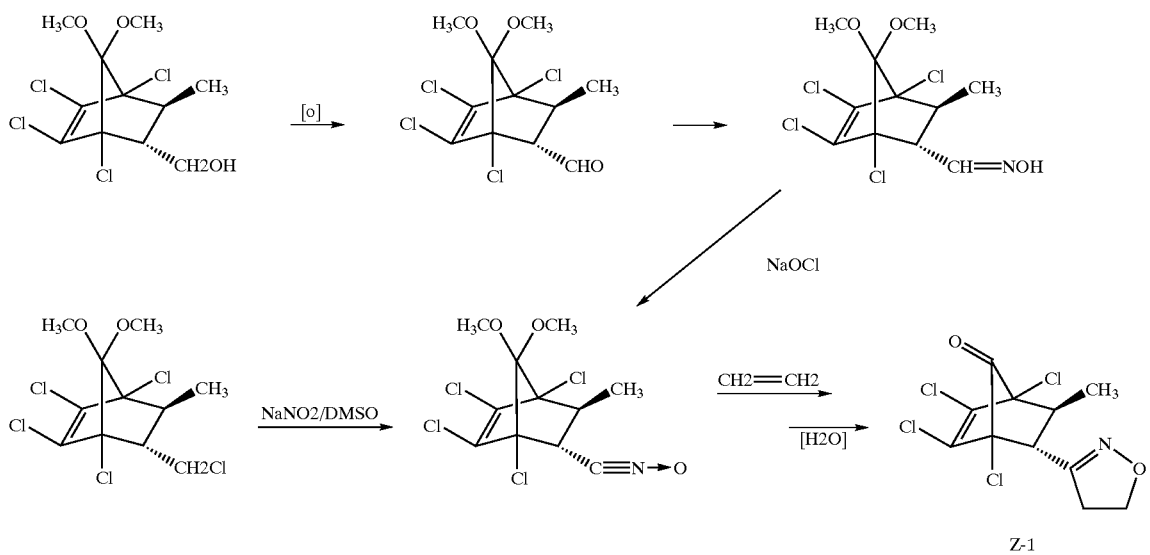

Furthermore, the compound where X is hydroxycarbonyl can be an intermediate for the syntheses of compounds that are difficult to synthesize from carboxylates. In addition, according to the methods of the present invention, Diels-Alder reactions can be carried out under milder conditions so as to be more practical than known methods using carboxylates.

What is claimed is:

1. A compound represented by Formula (1)

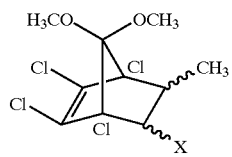
(1)

(wherein, X is hydroxycarbonyl, hydroxymethyl, halogenomethyl, nitromethyl or methylthiomethyl).

2. A process for the production of a compound of Formula (1)

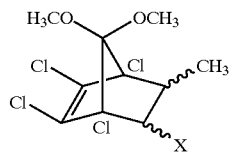
(1)

(wherein, X is hydroxycarbonyl, hydroxymethyl, halogenomethyl, nitromethyl or methylthiomethyl) by a reaction of 5,5-dimethoxy-1,2,3,4-tetrachlorocyclopentadiene with a compound of Formula (2)

$$CH_3CH=CH-X \qquad (2)$$

(wherein X is as defined above).

3. Trans-1,4,5,6-tetrachloro-3-methyl-7,7-dimethoxybicyclo[2.2.1]hept-5-ene-2-carboxylic acid.

4. Cis-1,4,5,6-tetrachloro-3-methyl-7,7-dimethoxybicyclo[2.2.1]hept-5-ene-2-carboxylic acid.

5. A process for the production of trans-1,4,5,6-tetrachloro-3-methyl-7,7-dimethoxybicyclo[2.2.1]hept-5-ene-2-carboxylic acid by reacting (E)-2-butenic acid with 5,5-dimethoxy-1,2,3,4-tetrachlorocyclopentadiene and isolating the product from the obtained adducts.

6. A process for the production of cis-1,4,5,6-tetrachloro-3-methyl-7,7-dimethoxybicyclo[2.2.1]hept-5-ene-2-carboxylic acid by reacting (Z)-2-butenic acid with 5,5-dimethoxy-1,2,3,4-tetrachlorocyclopentadiene and isolating the product from the obtained adducts.

* * * * *

UNITED STATES PATENT AND TRADEMARK OFFICE
CERTIFICATE OF CORRECTION

PATENT NO.    : 6,420,612 B1
DATED         : July 16, 2002
INVENTOR(S)   : Tomio Yagihara et al.

It is certified that error appears in the above-identified patent and that said Letters Patent is hereby corrected as shown below:

Title page,
Item [75], Inventors, replace "both of Odawara (JP)" with -- both of Kanagawa (JP) --.

Column 2,
Line 18, replace "and (1S, 4R, SR, 6R)" with -- and (1S, 4R, 5R, 6R) --.

Column 6,
Line 8, replace "6-methyl-trans-5-chloromethyl-7,71-" with -- 6-methyl-trans-5-chloromethyl-7,7'- --.
Line 60, replace "nitrite" with -- nitrile --.
Line 66, replace "nitrite" with -- nitrile --.

Signed and Sealed this

Nineteenth Day of November, 2002

*Attest:*

JAMES E. ROGAN
*Attesting Officer*   *Director of the United States Patent and Trademark Office*